(12) United States Patent
Tsubata et al.

(10) Patent No.: US 9,192,843 B2
(45) Date of Patent: Nov. 24, 2015

(54) ANALYSIS SYSTEM, ANALYSIS APPARATUS, ELECTRONIC DEVICE, ANALYSIS METHOD, AND PROGRAM

(71) Applicants: Seiko Instruments Inc., Chiba-shi, Chiba (JP); Keio University, Minato-ku, Tokyo (JP)

(72) Inventors: Keisuke Tsubata, Chiba (JP); Akira Takakura, Chiba (JP); Yuji Ohgi, Fujisawa (JP)

(73) Assignee: Keio University (JP)

( * ) Notice: Subject to any disclaimer, the term of this patent is extended or adjusted under 35 U.S.C. 154(b) by 87 days.

(21) Appl. No.: 14/011,392

(22) Filed: Aug. 27, 2013

(65) Prior Publication Data
US 2014/0062681 A1 Mar. 6, 2014

(30) Foreign Application Priority Data

Aug. 28, 2012 (JP) .................. 2012-188089
Aug. 28, 2012 (JP) .................. 2012-188090
Jul. 2, 2013 (JP) .................. 2013-139188

(51) Int. Cl.
| | |
|---|---|
| *A63B 71/06* | (2006.01) |
| *A61B 5/11* | (2006.01) |
| *A63B 24/00* | (2006.01) |
| *A61B 5/00* | (2006.01) |

(52) U.S. Cl.
CPC .......... *A63B 71/0686* (2013.01); *A61B 5/1123* (2013.01); *A63B 24/0062* (2013.01); *A63B 71/0605* (2013.01); *A61B 5/6831* (2013.01); *A61B 2562/0219* (2013.01); *A63B 2024/0071* (2013.01); *A63B 2220/40* (2013.01); *A63B 2220/836* (2013.01); *A63B 2225/20* (2013.01); *A63B 2225/50* (2013.01); *A63B 2244/20* (2013.01)

(58) Field of Classification Search
CPC ........... A63B 71/0786; A63B 71/0605; A63B 71/0685; A63B 24/0063; A63B 2220/40
USPC .................. 340/323 R; 700/91; 482/55.8
See application file for complete search history.

(56) References Cited

U.S. PATENT DOCUMENTS

2010/0030482 A1\* 2/2010 Li .................................. 702/19

FOREIGN PATENT DOCUMENTS

JP 2005-152496 A 6/2005

\* cited by examiner

*Primary Examiner* — Steven Lim
*Assistant Examiner* — Hongmin Fan
(74) *Attorney, Agent, or Firm* — Brinks Gilson & Lione (57) ABSTRACT

An analysis system includes: an electronic device that is attached to an upper body of a swimmer; and an analysis apparatus. The electronic device includes: an acceleration sensor that detects acceleration in a gravity direction in a state where the swimmer stands erect; and a first communication unit that transmits acceleration data indicating the acceleration detected by the acceleration sensor to the analysis apparatus. The analysis apparatus includes: a second communication unit that receives the acceleration data from the electronic device; and a control unit that determines whether the swimmer is in a swimming state or the swimmer is in a resting state, based on the acceleration data received by the second communication unit.

19 Claims, 5 Drawing Sheets

ANALYSIS SYSTEM, ANALYSIS APPARATUS, ELECTRONIC DEVICE, ANALYSIS METHOD, AND PROGRAM

RELATED APPLICATIONS

This application claims priority under 35 U.S.C. §119 to Japanese Patent Application Nos. 2012-188089 filed on Aug. 28, 2012, 2012-188090 filed on Aug. 28, 2012, and 2013-139188 filed on Jul. 2, 2013, the entire contents of which are hereby incorporated by reference.

BACKGROUND OF THE INVENTION

1. Field of the Invention

The present invention relates to an analysis system, an analysis apparatus, an electronic device, an analysis method, and a program.

2. Description of the Related Art

In the past, a technology is known that distinguishes a swim state and a resting state by an acceleration signal when swimming in a state where an acceleration sensor is attached to the body (for example, refer to Japanese Unexamined Patent Application, First Publication No. 2005-152496). In the related art described in Japanese Unexamined Patent Application, First Publication No. 2005-152496, a state where an acceleration signal having regularity is output from an acceleration sensor is determined to be a swimming state, and if the output of the acceleration signal has been stopped for a predetermined length of time, it is determined that swimming is finished.

SUMMARY OF THE INVENTION

However, in the related art described in Japanese Unexamined Patent Application, First Publication No. 2005-152496, even though in a state where the swimmer is not swimming, the acceleration sensor, in some cases, outputs a sensor signal similar to that output in a state where the swimmer is swimming. For example, if the acceleration sensor is attached to the wrist and the arm is moved after finishing the swimming, there is a possibility that the state where the swimmer is not swimming cannot be detected. In other words, it is difficult to accurately determine whether there is a state where the swimmer is swimming or there is a state where the swimmer is not swimming.

In addition, when finishing swimming in a pool, the swimmer touches the wall and the swimming is finished, however, specifically at the time of exercise, there is a case where the swimmer touches the wall after keeping gliding motion for a while, or a case where the swimmer does not expressly touch the wall. In such cases, since the changing point of the acceleration signal tends to be unclear, it is difficult to reliably detect the timing when swimming is finished (when the swimmer touched a goal) by the related art described in Japanese Unexamined Patent Application, First Publication No. 2005-152496.

Some aspects of the present invention have an object to provide an analysis system, an analysis apparatus, an electronic device, an analysis method, and a program that are capable of accurately determining whether there is a state where a swimmer is swimming or there is a state where a swimmer is not swimming. Other aspects of the present invention have an object to provide an analysis system, an analysis apparatus, an electronic device, an analysis method, and a program that are capable of accurately detecting the timing when a swimmer touched a wall.

An analysis system according to an aspect of the present invention includes: an electronic device that is attached to an upper body of a swimmer; and an analysis apparatus, wherein the electronic device includes: an acceleration sensor that detects acceleration in a direction that becomes a gravity direction when the swimmer stands erect; and a first communication unit that transmits acceleration data indicating the acceleration detected by the acceleration sensor to the analysis apparatus, and wherein the analysis apparatus includes: a second communication unit that receives the acceleration data from the electronic device; and a state determination unit that determines whether the swimmer is in a swimming state or the swimmer is in a resting state, based on the acceleration data received by the second communication unit.

DETAILED DESCRIPTION OF THE PREFERRED EMBODIMENTS (First Embodiment)

Figure 1:
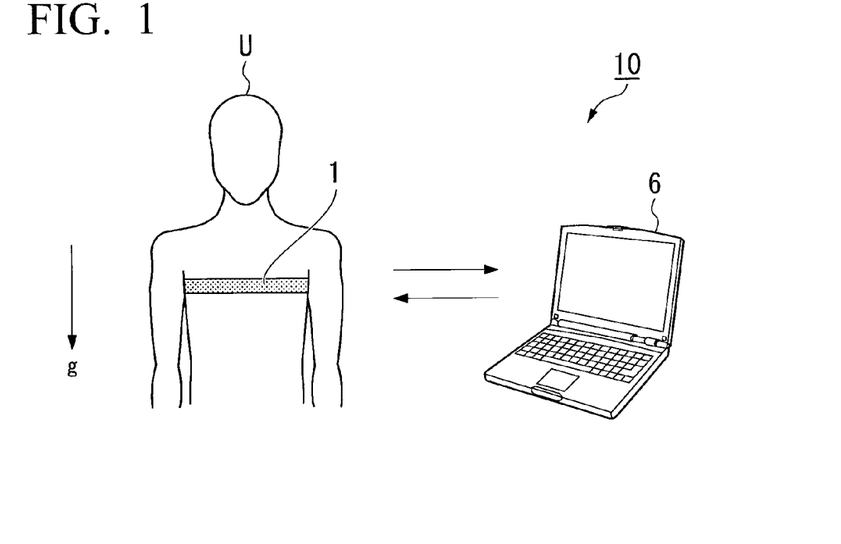
FIG. 1 is a system structural view that shows a structure of an analysis system according to a first embodiment of the present invention.

Hereinafter, a first embodiment of the present invention will be described with reference made to the appended drawings. FIG. 1 is a system structural view that shows a structure of an analysis system 10 according to the present embodiment. The analysis system 10 is a system that analyses, provided that a wearer U (swimmer) is doing interval training, whether the wearer U is in a state where the wearer U is swimming (a swimming state), or in a state where the wearer U is not swimming (a resting state).

An explanation is made below with reference to an example of an interval training in which sixteen repeats of fifty meters are performed at a one-minute cycle time. The wearer U performs a set of swimming fifty meters and resting sixteen times. At this time, the wearer U takes a rest such that the amount of time for one set is one minute. Namely, the wearer U starts a second repeat one minute after the start of a first bout.

In an example shown in the figure, the analysis system 10 is configured to include an electronic device 1 and an analysis apparatus 6. The electronic device 1 and the analysis apparatus 6 perform transmitting and receiving data by wireless communications, for example, such as a wireless LAN (Local Area Network), the Bluetooth (registered trademark), and the Zigbee (registered trademark). The electronic device 1 is a device that is attached to an upper body of the wearer U and detects acceleration. The electronic device 1 is provided with a three-axis acceleration sensor that has, in a state where the wearer U is wearing the electronic device 1 and standing erect, an axis in a direction that is a gravity direction, an axis in a direction perpendicular to the breast, and an axis in a direction parallel with the breast.

The electronic device 1 transmits acceleration data indicating acceleration that is detected by an acceleration sensor, to the analysis apparatus 6. For example, the electronic device 1 transmits acceleration data indicating a change of acceleration during the period of time from the beginning of detection of acceleration to the end of detection of acceleration, to the analysis apparatus 6. The timing when the electronic device 1 transmits the acceleration data is when the detection of the acceleration data is ended, when a command to transmit the acceleration data is input, and the like. Alternatively, the electronic device 1 may transmit acceleration data indicating the detected acceleration, at any time during detection of acceleration.

The analysis apparatus 6 is configured by a computer, and analyzes a state of swimming of the wearer U, based on the acceleration data received from the electronic device 1. For example, the analysis apparatus 6 determines whether the state of the wearer U is the swimming state or is the resting state, based on the acceleration data.

Figure 2:
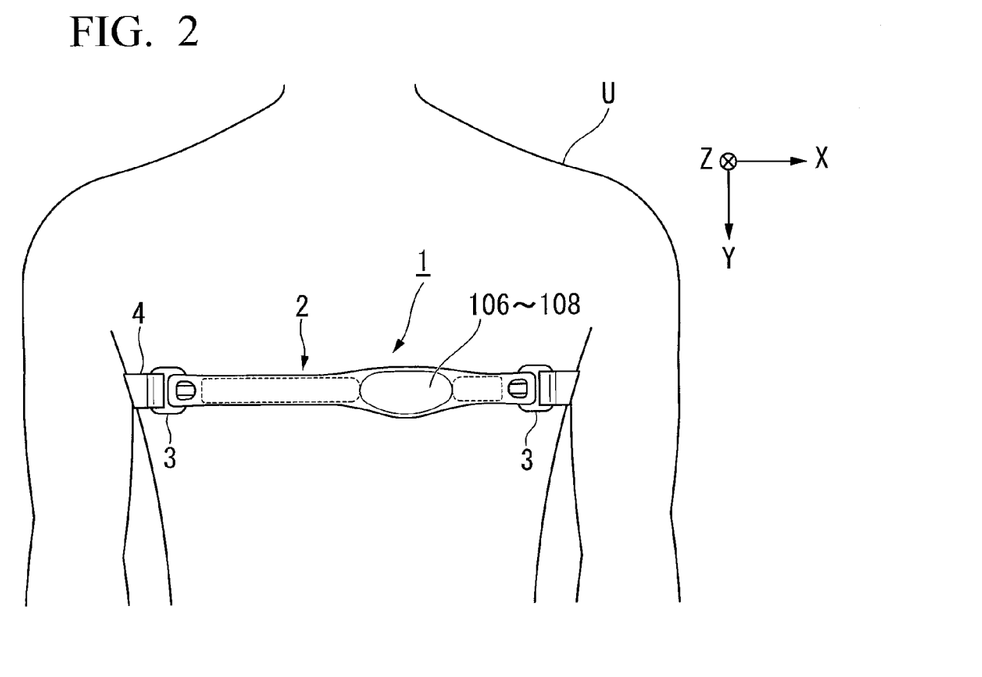
FIG. 2 is an outline view that shows an appearance of an electronic device according to the first embodiment of the present invention.

Next, a structure of the electronic device 1 is explained. FIG. 2 is an outline view that shows an appearance of the electronic device 1 according to the present embodiment. In an example shown in the figure, the electronic device 1 is attached to a breast portion that is a surface of a biological body of the wearer U so as to detect acceleration, and transmits an acceleration signal indicating this detected acceleration to the analysis apparatus 6. The electronic device 1 is provided with a sensor unit 2 and a backside belt 4 that is attached to both ends of this sensor unit 2 via a connection member 3. The backside belt 4 is formed so as to be capable of surrounding the entire circumference of the breast portion of the wearer U in cooperation with the sensor unit 2.

The sensor unit 2 has a case formed so as to be elongated in a circumferential direction of the breast portion of the wearer U, and this case accommodates acceleration sensors 106 to 108. The acceleration sensors 106 to 108 detect the X component, the Y component, and the Z component of orthogonal coordinate axes that are orthogonal to one another, and output an acceleration signal with an intensity corresponding to the acceleration of each of the components.

In this embodiment, the longer direction of the case is defined as the X-axis direction, the shorter direction of the case is defined as the Y-axis direction, and the thickness direction of the case is defined as the Z-axis direction. In a state where the wearer U wears the electronic device 1 and stands erect, the direction parallel to the breast (direction from left to right in the figure) is the X-axis direction, the gravity direction perpendicular to the X-axis direction (direction from upper to lower in the figure) is the Y-axis direction, and the back-to-belly direction perpendicular to the XY plane (direction from the breast to the back) is the Z-axis direction.

In this embodiment, the acceleration sensor 106 detects acceleration X in the X-axis direction. The acceleration sensor 107 detects acceleration Y in the Y-axis direction. The acceleration sensor 108 detects acceleration Z in the Z-axis direction.

Note that the acceleration sensors 106 to 108 in the electronic device 1 are provided within the case, and when the electronic device 1 is worn on the breast portion of the wearer U, the position of the acceleration sensors 106 to 108 is made to be a position displaced to any one of the left side and the right side from the center of the breast portion of the wearer U.

The acceleration sensors 106 to 108, for example, may be configured by a MEMS (Micro Electro Mechanical Systems) three-axis acceleration sensor. The acceleration sensors 106 to 108 may be configured by three one-axis acceleration sensors arranged in three axes directions that are orthogonal to one another.

Figure 3:
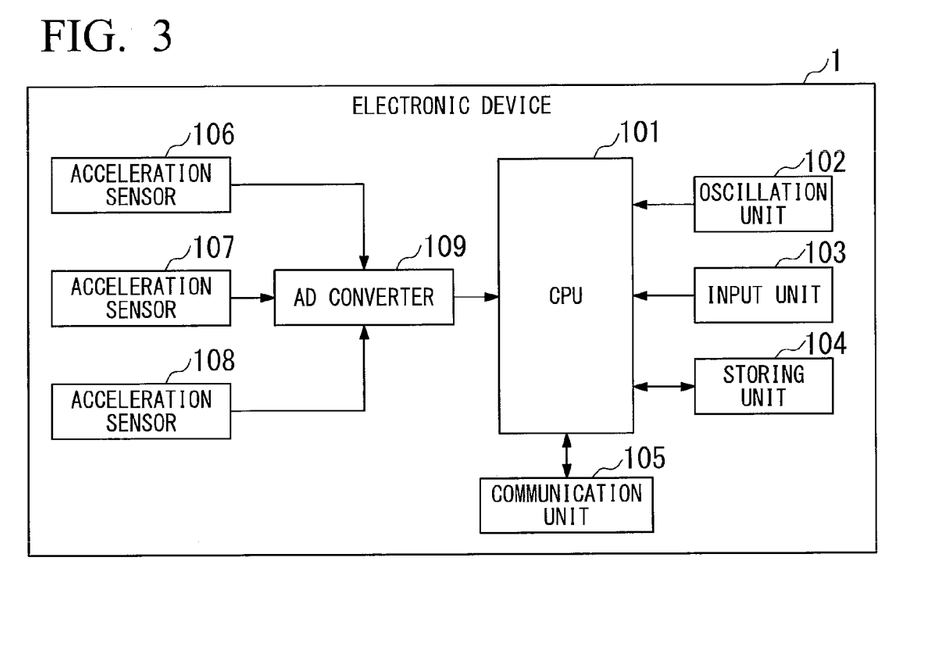
FIG. 3 is a block diagram that shows a structure of the electronic device according to the first embodiment of the present invention.

FIG. 3 is a block diagram that shows a structure of the electronic device 1 according to the present embodiment. In an example shown in the figure, the electronic device 1 is provided with a CPU (Central Processing Unit) 101, an oscillation unit 102, an input unit 103, a storing unit 104, a communication unit 105 (first communication unit), the acceleration sensors 106 to 108, and an AD (Analog to Digital) converter 109.

The CPU 101 performs control of each unit provided in the electronic device 1. The oscillation unit 102 outputs a reference clock signal for the operation of the CPU 101. The input unit 103 accepts an input of a command from the wearer U. For example, the input unit 103 accepts an input of a command to begin the detection of acceleration, or a command to end the detection of acceleration. In addition, the input unit 103 accepts an input of a command to transmit acceleration data indicating acceleration detected by the acceleration sensors 106 to 108 to the analysis apparatus 6.

The storing unit 104 stores a program executed by the CPU 101, data required during the processes performed by each of the units provided in the electronic device 1, and the like. In addition, the storing unit 104 stores acceleration data indicating acceleration detected by the acceleration sensors 106 to 108.

In addition, the CPU 101 may execute a program for performing a state determination and realize a state determination function as a function of the electronic device 1. Specifically, the program for performing the state determination may be stored in the storing unit 104 or a memory that is not shown in the figure, and the CPU 101 may read out and execute the program, thereby realizing the state determination function. In this case, the electronic device 1 can be considered to include a state determination unit that performs a state determination.

Moreover, the CPU 101 may execute a program for performing a turn determination and realize a turn determination function as a function of the electronic device 1. Specifically, the program for performing the turn determination may be stored in the storing unit 104 or a memory that is not shown in the figure, and the CPU 101 may read out and execute the program, thereby realizing the turn determination function. In this case, the electronic device 1 can be considered to include a turn determination unit that performs a turn determination.

Furthermore, the CPU 101 may execute a program for performing a start determination and realize a start determination function as a function of the electronic device 1. Specifically, the program for performing the start determination may be stored in the storing unit 104 or a memory that is not shown in the figure, and the CPU 101 may read out and execute the program, thereby realizing the start determination function. In this case, the electronic device 1 can be considered to include a start determination unit that performs a start determination.

Furthermore, the CPU 101 may execute a program for performing a touch determination and realize a touch determination function as a function of the electronic device 1. Specifically, the program for performing the touch determination may be stored in the storing unit 104 or a memory that is not shown in the figure, and the CPU 101 may read out and execute the program, thereby realizing the touch determination function. In this case, the electronic device 1 can be considered to include a touch determination unit that performs a touch determination.

Note that an example of the memory in which each program is stored and which is not shown in the figure may be a memory, which is an external memory of the electronic device 1 and from which the CPU 101 can read out the program.

The communication unit 105 performs wireless communication with the analysis apparatus 6. For example, the communication unit 105 transmits acceleration data indicating acceleration detected by the acceleration sensors 106 to 108 to the analysis apparatus 6. The acceleration sensors 106 to 108 detect the X component, the Y component, and the Z component of orthogonal coordinate axes that are orthogonal to one another, and output an acceleration signal with an intensity corresponding to acceleration of each component. The AD converter 109 converts the acceleration signal output by the acceleration sensors 106 to 108 into a digital signal.

Figure 4:
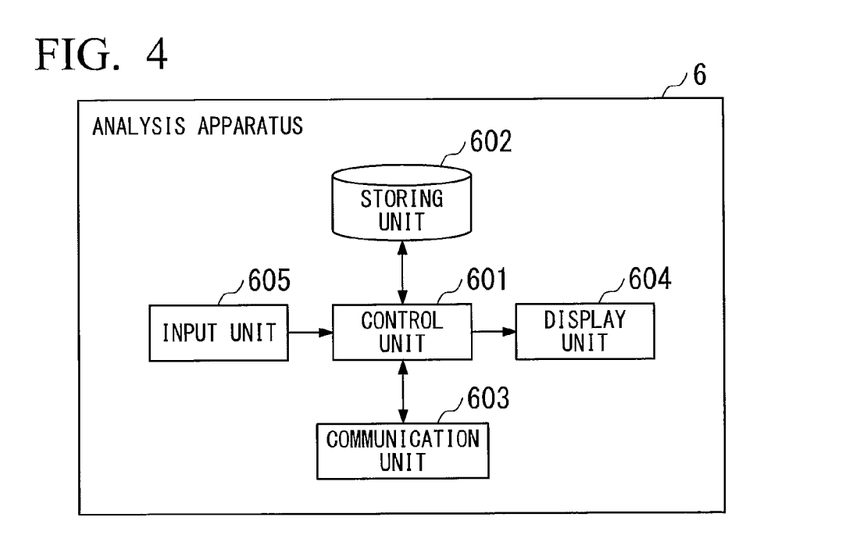
FIG. 4 is a block diagram that shows a structure of an analysis apparatus according to the first embodiment of the present invention.

Next, a structure of the analysis apparatus 6 is explained. FIG. 4 is a block diagram showing a structure of the analysis apparatus 6 according to the present embodiment. In an example shown in the figure, the analysis apparatus 6 is provided with a control unit 601 (state determination unit, start determination unit, turn determination unit, touch determination unit), a storing unit 602, a communication unit 603 (second communication unit), a display unit 604, and an input unit 605.

The control unit 601 performs control of each unit provided in the analysis apparatus 6. For example, the control unit 601 analyses whether the wearer U is in a state where the wearer U is swimming (a swimming state), or in a state where the wearer U is not swimming (a resting state). Specifically, the control unit 601 determines whether the wearer U is in a swimming state or is in a resting state, based on acceleration data received from the electronic device 1. More specifically, the control unit 601 determines that the wearer U is in a resting state if the acceleration Y in the Y-axis direction has been within a predetermined range close to the acceleration of gravity (1G or −1G) for more than a predetermined length of time. Otherwise, the control unit 601 determines that the wearer U is in a swimming state.

In addition, the control unit 601 determines the timing when the wearer U started and the timing when the wearer U turned, based on acceleration data received from the electronic device 1. Specifically, the control unit 601 determines the timing when the absolute value of the acceleration Y becomes greater than a predetermined value immediately after the acceleration Y gets close to zero from the acceleration of gravity (1G or −1G) after having determined that the wearer U is in a resting state, as the start timing. In addition, the control unit 601 determines that the timing when the absolute value of the acceleration Y becomes greater than a predetermined value in the case that the wearer U has been determined to be in a swimming state, as the turning timing.

In addition, the control unit 601 determines the timing when the wearer U touched (touched a wall), from a time interval in which the wearer U was determined to be in a swimming state, based on the acceleration data received from the electronic device 1. Specifically, the control unit 601 traces the acceleration data back from the time when the wearer U shifted from a swimming state to a resting state, and determines the timing when the acceleration becomes equal to or less than a predetermined value as the timing of a goal touch.

The storing unit 602 stores acceleration data received from the electronic device 1, the state of the wearer U analyzed by the control unit 601, and the like. In addition, the storing unit 602 stores a program executed by the control unit 601, data required during the processes performed by each unit provided in the analysis apparatus 6, and the like. The communication unit 603 performs wireless communication with the electronic device 1. For example, the communication unit 603 receives acceleration data from the electronic device 1. The display unit 604 is a display device such as a liquid crystal display (LCD) that displays a character, a graphic, and the like. The input unit 605 accepts an input of a command from the wearer U.

Figure 5:
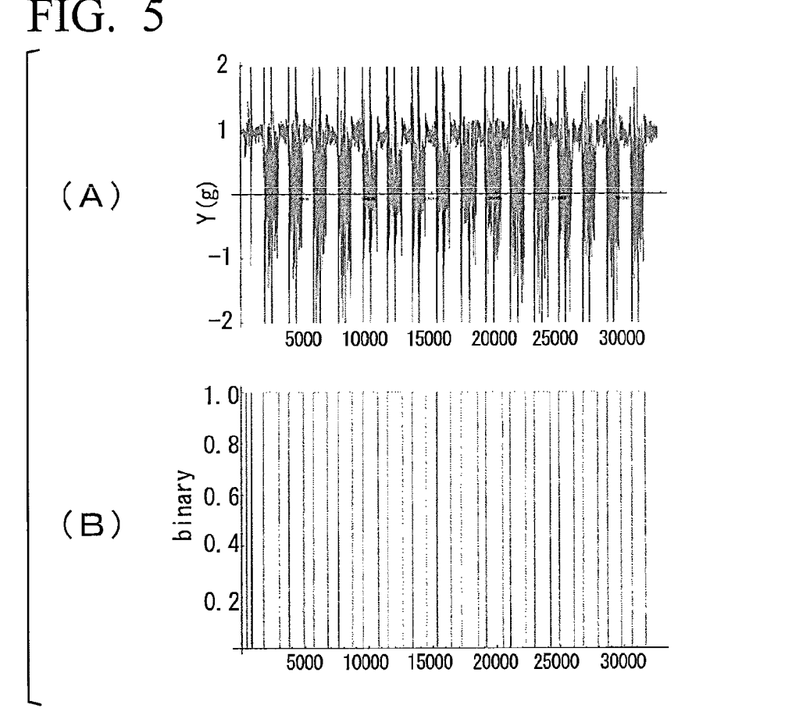
FIG. 5 is a graph for explaining a process that is performed by the analysis apparatus according to the first embodiment of the present invention, so as to determine whether a swimmer is in a swimming state or a swimmer is in a resting state.
Figure 6:
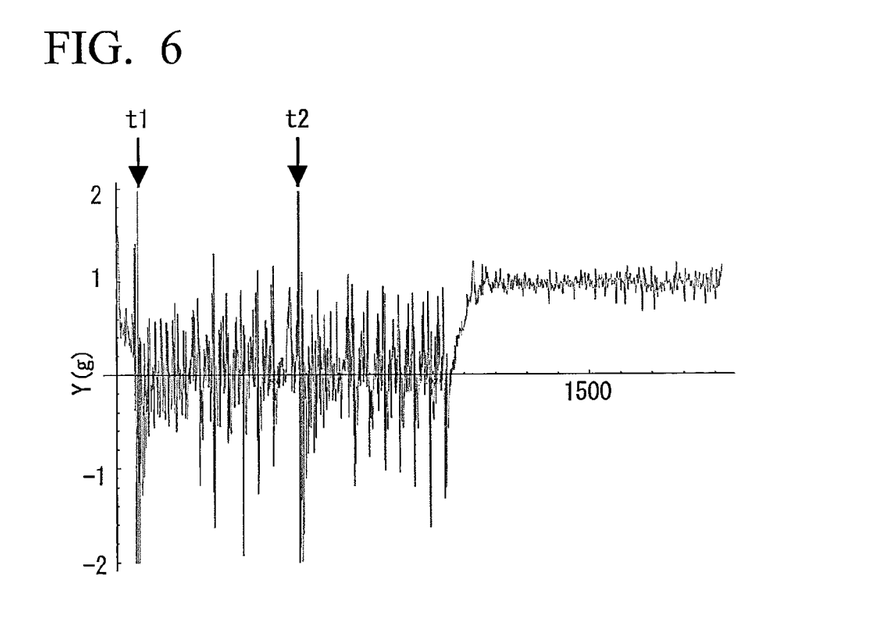
FIG. 6 is a graph for explaining a process that is performed by the analysis apparatus according to the first embodiment of the present invention, so as to determine the starting time and the turning time.
Figure 7:
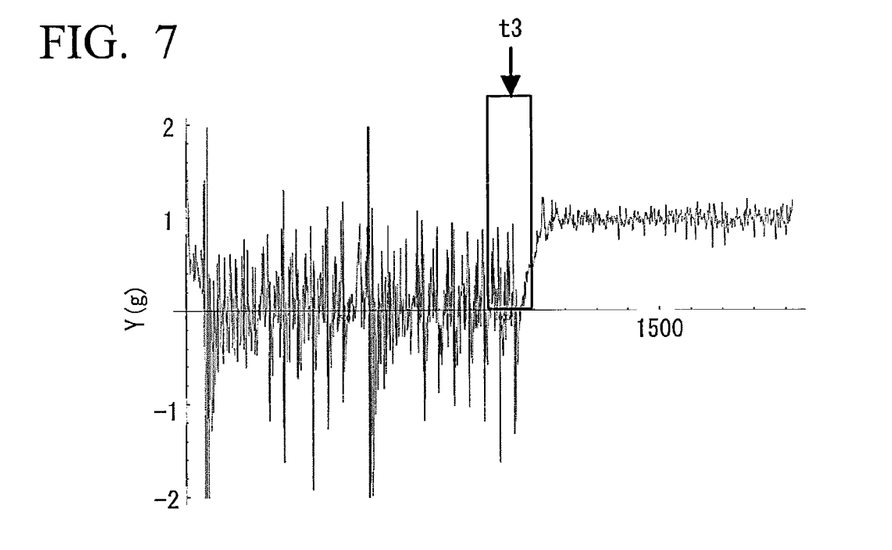
FIG. 7 is a graph for explaining a process that is performed by the analysis apparatus according to the first embodiment of the present invention, so as to determine the timing of touch.

Next, referring to FIG. 5 to FIG. 7, explanations are made as to a method for analyzing whether the wearer U is in a swimming state or is in a resting state, and a method for analyzing a start timing, a turn timing, and a goal touch (touch a wall) timing of the wearer U, by the analysis apparatus 6.

FIG. 5 is a graph for explaining a process that is performed by the analysis apparatus 6 in the present embodiment, so as to determine whether the wearer U is in a swimming state or is in a resting state. The graph shown in FIG. 5(A) is a graph showing a temporal change of the acceleration Y in the Y-axis direction. The vertical axis of the graph shown in FIG. 5(A) indicates acceleration Y in the Y-axis direction, and the horizontal axis indicates a time. In an example shown in the figure, the value of the horizontal axis is multiples of a sampling rate of the acceleration signal, and thirty two corresponds to one second.

The graph shown in FIG. 5(B) is a graph showing binary data of FIG. 5(A). The value in the vertical axis of the graph shown in FIG. 5(B) is zero in the case that the acceleration Y in the graph shown in FIG. 5(A) is close to the acceleration of gravity (1G or −1G) (namely, $1-\alpha \leq Y < 1+\alpha$ (or, $-1-\alpha < Y \leq -1+\alpha$)), and otherwise (namely, $Y < 1-\alpha$ or $Y \geq 1+\alpha$ (or, $Y \leq -1-\alpha$ or $Y > -1+\alpha$)) the value is one. The $\alpha$ is a predetermined positive constant such as, for example, $\alpha = 0.02$.

In the case that the wearer U is in a swimming state, since the sensitivity axis of the acceleration sensor 107 faces in the horizontal direction, the DC component of the acceleration Y in the Y-axis direction becomes a value around 0G. On the other hand, in the case that the wearer U is in a resting state, since the wearer U stands up, the DC component of the acceleration Y in the Y-axis direction becomes a value around the acceleration of gravity (1G or −1G). Therefore, in the graph shown in FIG. 5(B), the control unit 601 determines the period of time in which the acceleration in the Y-axis direction has been zero for more than a predetermined length of time (for example, one second) as a swimming state, and determines the other period of time as a resting state. In other words, the control unit 601 determines the period of time in which the acceleration Y in the Y-axis direction has been a value around 1G (or −1G) for more than a predetermined length of time (for example, one second) as a resting state, and determines the other period of time as a swimming state.

FIG. 6 is a graph for explaining a process that is performed by the analysis apparatus 6 in the present embodiment, so as to determine a start timing and a turn timing of the wearer U. The graph shown in the figure is a graph showing a temporal change of the acceleration Y in the Y-axis direction. The vertical axis of the graph indicates acceleration Y in the Y-axis direction, and the horizontal axis indicates a time. In an example shown in the figure, the value of the horizontal axis is multiples of a sampling rate of the acceleration signal, and thirty two corresponds to one second.

When the wearer U performs the start or the turn, high acceleration occurs in the Y-axis direction.

Therefore, the control unit 601 determines a time 't1' when the absolute value of the acceleration Y becomes greater than a predetermined value (for example, 1.98 G) immediately after the acceleration Y gets close to zero from the acceleration of gravity (1G or −1G) after having determined that the wearer U is in a resting state, as the start timing. In addition, the control unit 601 determines a time 't2' when the absolute value of the acceleration Y becomes greater than a predetermined value (for example, 1.98 G) in the case that the wearer U is in a swimming state, as the turning timing of the wearer U.

Note that, in this embodiment, the control unit 601 determines the timing when the absolute value of the acceleration Y becomes greater than a predetermined value immediately after the acceleration Y gets close to zero from the acceleration of gravity (1G or −1G) after having determined that the wearer U is in a resting state, as the start timing. However, the method is not limited thereto, for example, if the wearer U performs an interval training, a time when the wearer U starts may be preliminarily estimated.

Specifically, the wearer U is performing an interval training in which a swimming state and a resting state are alternately repeated at one-minute intervals. In this case, the wearer U starts one minute after beginning to take a rest. Therefore, it is possible to pre-estimate a time interval (hereinafter, referred to as a start interval) in which the wearer U is supposed to start. For example, it is possible to set the period of time from fifty eight second to sixty two second after the wearer U becomes a resting state, as a start interval. In this case, the control unit 601 determines that a time when the absolute value of the acceleration Y becomes greater than a predetermined value within the pre-estimated start interval is the start timing.

FIG. 7 is a graph for explaining a process that is performed by the analysis apparatus 6 in the present embodiment, so as to determine a goal touch timing. The graph shown in the figure is a graph showing a temporal change of the acceleration Y in the Y-axis direction. Note that the vertical axis of the graph indicates acceleration Y in the Y-axis direction, and the horizontal axis indicates a time. In an example shown in the figure, the value of the horizontal axis is multiples of a sampling rate of the acceleration signal, and thirty two corresponds to one second.

When the wearer U is in a swimming state, since the sensitivity axis of the acceleration sensor 107 faces in the horizontal direction, the DC component of the acceleration in the Y-axis direction becomes a value around 0G. In addition, since the wearer U gradually stands up after finishing swimming and touching the wall, the DC component of the acceleration in the Y-axis direction gradually changes from 0G to the acceleration of gravity (1G or −1G). Therefore, the control unit 601 traces back the acceleration data from the timing when the acceleration Y in the Y-axis direction becomes the acceleration of gravity (1G or −1G) (a timing when the state shifts from a swimming state to a resting state), and determines a time 't3' at which the acceleration Y in the Y-axis direction intersects with 0G, as a goal touch timing.

Specifically, first, the control unit 601 sets a time interval a predetermined length of time (for example, four seconds) prior to the timing when the state shifts from a swimming state to a resting state, to be an estimated touch interval in which the touch is supposed to be performed. Subsequently, because the output from the acceleration sensor 107 includes noise, the control unit 601 performs filtering by a predetermined frequency and smoothing the acceleration Y in the estimated touch interval. Then, the control unit 601 traces back the estimated touch interval, and determines the timing when the acceleration Y after filtering becomes equal to or less than a predetermined value (for example, 0G) (when the acceleration Y after filtering becomes around zero), as the touch time.

Figure 8:
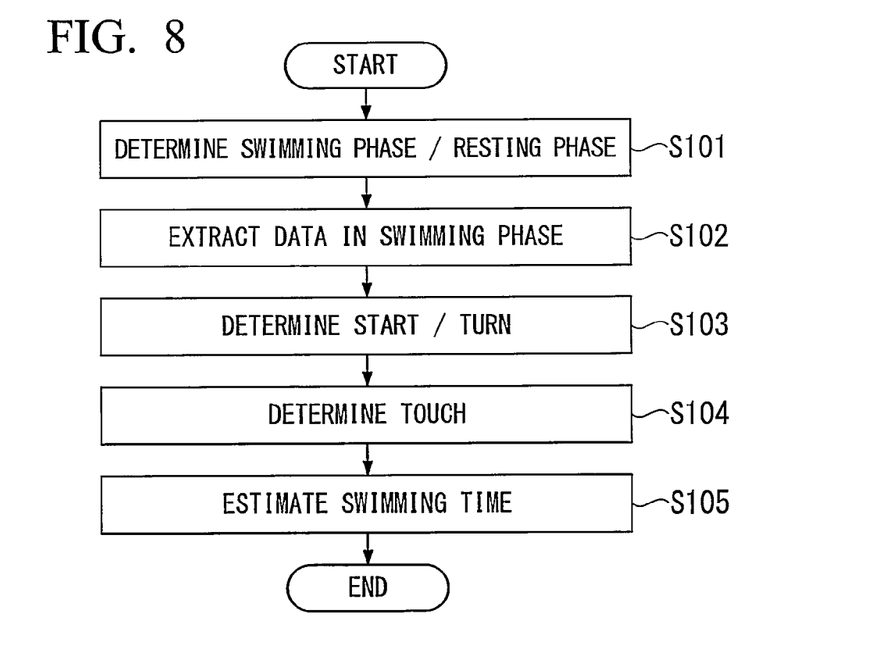
FIG. 8 is a flowchart that shows a process sequence of an analysis process, performed by the analysis apparatus according to the first embodiment of the present invention.

Next, an explanation is made as to a process sequence in which the analysis apparatus 6 analyzes whether the wearer U is in a swimming state or is in a resting state. FIG. 8 is a flowchart showing a process sequence of an analysis process, performed by the analysis apparatus 6 in the present embodiment. The analysis apparatus 6 receives in advance acceleration data during the training of the wearer U from the electronic device 1, and stores the data in the storing unit 602. Then, the control unit 601 reads out the acceleration data stored in the storing unit 602, and performs the following processes based on the acceleration data that is read out.

(Step S101) The control unit 601 determines a swimming phase and a resting phase, based on the acceleration data. The swimming phase is a period of time in a swimming state, and the resting phase is a period of time in a resting state.

Specifically, the control unit 601 reads out acceleration Y from the acceleration data, and sets a period of time in which the acceleration Y that is read out is continuously close to the acceleration of gravity for more than one second, as the resting phase. The control unit 601 sets a period of time other than the resting phase as the swimming phase. Then, the process proceeds to step S102.

(Step S102) The control unit 601 extracts the acceleration data in the swimming phase determined. Specifically, a time-series product of acceleration data in the Y-axis direction and the binary data of the acceleration data is calculated. Thereby, only the acceleration data in the swimming phase is extracted. Then, the process proceeds to step S103.

(Step S103) The control unit 601 determines a start timing and a turn timing, based on the extracted acceleration data in the swimming phase. Specifically, the control unit 601 determines a time when the absolute value of the acceleration Y becomes greater than a predetermined value (for example, 1.98 G) immediately after the acceleration Y gets close to zero from the acceleration of gravity (1G or −1G) after having determined that the wearer U is in a resting state, as a start timing. In addition, the control unit 601 determines a time when the absolute value of the acceleration Y becomes greater than a predetermined value (for example, 1.98 G) in the case that the wearer U is in a swimming state, as a turn timing. Then, the process proceeds to step S104.

(Step S104) The control unit 601 determines a goal touch timing, based on the extracted acceleration data in the swimming phase. Specifically, the control unit 601 traces back the acceleration data from the timing when the state is switched from a swimming state to a resting state, and determines a time at which the acceleration Y in the Y-axis direction intersects with 0G, as a touch timing. Then, the process proceeds to step S105.

(Step S105) The control unit 601 estimates a swimming time of the wearer U in each set. Specifically, the control unit 601 sets, in each set, a time difference between the start timing and the touch timing, as a swimming time. Then the process ends.

Note that, by using the acceleration data in the swimming phase, which is extracted in the process of step S102, a process that estimates a swim stroke of the wearer U, or a process that estimates a frequency of stroke may be performed.

As is described above, in the present embodiment, the electronic device 1 detects acceleration Y in a direction that becomes a gravity direction when the wearer U stands erect, and transmits the detected acceleration Y to the analysis apparatus 6. The analysis apparatus 6 determines whether the wearer U is in a swimming state or is in a resting state, based on the acceleration Y that is detected by the electronic device 1. Specifically, the analysis apparatus 6 determines that the wearer U is in a resting state if the acceleration Y has been within a predetermined range close to the acceleration of gravity for more than a predetermined length of time, and otherwise, determines that the wearer U is in a swimming state. Thereby, it is possible to accurately determine the swimming state and the resting state.

In addition, the analysis apparatus 6 determines that a time when the absolute value of the acceleration Y becomes greater than a predetermined value immediately after the acceleration Y gets close to zero from the acceleration of gravity (1G or −1G) after having determined that the wearer U is in a resting state is a start timing. In addition, the analysis apparatus 6 determines that a time when the absolute value of the acceleration Y becomes greater than a predetermined value during the period of time in which the wearer U is determined to be in a swimming state is a turn timing. Thus, because the start timing and the turn timing are identified based on the determination of the resting state or the swimming state, it is possible to further improve the accuracy to identify the start timing and the turn timing.

In addition, the analysis apparatus 6 traces back acceleration data from a time when the wearer U is determined to switch from a swimming state to a resting state, and determines that a time at which the value of acceleration Y intersects with zero is a goal touch timing. For example, in a method according to the related art, a changing point of an acceleration signal tends to be unclear, if a swimmer touches the wall after keeping a kick and stretch state for a while, or if a swimmer does not expressly touch the wall, and therefore there is a possibility that the touch timing cannot be determined. On the other hand, in the present embodiment, the analysis apparatus 6 determines a time when the wearer U shifted from a swimming state to a resting state (a time at which acceleration becomes close to the acceleration of gravity), which is easy to be determined more accurately, and determines the touch timing by tracing back the acceleration data from the determined time. Accordingly, the analysis apparatus 6 can determine the touch timing more accurately.

(Second Embodiment)

Next, a second embodiment of the present invention will be described with reference made to the appended drawings. In the first embodiment, the analysis apparatus 6 determines whether the wearer U is in a swimming state or is in a resting state. On the other hand, in this embodiment, the electronic device 1 determines whether the wearer U is in a swimming state or is in a resting state. The structure of the analysis system 10 in the present embodiment is the same as that in the first embodiment.

The difference between the present embodiment and the first embodiment is that the CPU 101 (state determination unit) of the electronic device 1 determines whether the wearer U is in a swimming state or is in a resting state, based on the acceleration Y detected by the acceleration sensor 107. Specifically, the CPU 101 determines that the wearer U is in a resting state if the acceleration Y in the Y-axis direction has been within a predetermined range close to the acceleration of gravity (1G or −1G) for more than a predetermined length of time, and otherwise, determines that the wearer U is in a swimming state.

In addition, the difference between the present embodiment and the first embodiment is that the CPU 101 (start determination unit) determines that a time when the absolute value of the acceleration Y becomes greater than a predetermined value immediately after the acceleration Y gets close to zero from the acceleration of gravity (1G or −1G) after having determined that the wearer U is in a resting state is a start timing, and determines that a time at which the absolute value of the acceleration Y becomes greater than a predetermined value while the wearer U is in a swimming state is a turn timing.

In addition, the difference between the present embodiment and the first embodiment is that the CPU 101 (touch determination unit) determines a timing when the wearer U touched (touched a wall), based on the acceleration data received from the acceleration sensor 107. Specifically, the CPU 101 traces back the acceleration data from the time when the wearer U shifted from a swimming state to a resting state, and determines the time when the acceleration becomes equal to or less than a predetermined value (for example, 0G) as a timing of the goal touch.

In addition, the difference between the present embodiment and the first embodiment is that the analysis apparatus 6 (external device) has two operation modes which are a power saving mode in which consumption of electric power is reduced, and a normal mode.

Figure 9:
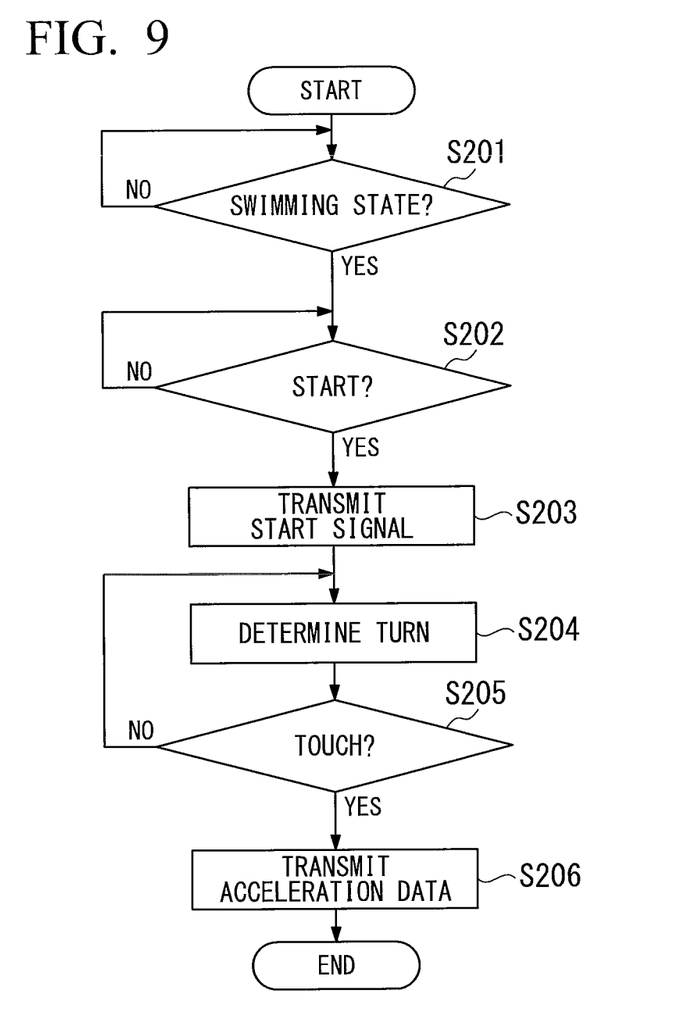
FIG. 9 is a flowchart that shows a process sequence of an analysis process, performed by an electronic device according to a second embodiment of the present invention.

Hereinafter, an explanation of an analysis process in which the electronic device 1 in the present embodiment analyzes a state of swimming of the wearer U is provided. FIG. 9 is a flowchart showing a process sequence of the analysis process, performed by the analysis apparatus 6 in the present embodiment.

(Step S201) The CPU 101 determines whether or not the wearer U is in a swimming state, based on the acceleration detected by the acceleration sensor 107. The method for determining a swimming state is the same as that in the first embodiment. The routine proceeds to a process in step S202 if the CPU 101 has determined that the wearer U is in a swimming state. The routine returns to a process in step S201 if the CPU 101 has determined that the wearer U is not in a swimming state (the wearer U is in a resting state).

(Step S202) The CPU 101 determines whether or not the wearer U started, based on the acceleration detected by the acceleration sensor 107. The method of determining whether or not the wearer U started is the same as that in the first embodiment. The routine proceeds to a process in step S203 if the CPU 101 has determined that the wearer U has started, and otherwise (if the CPU 101 has determined that the wearer U has not started), the process in step S202 is performed again.

(Step S203) The CPU 101 transmits a start signal indicating that the wearer U has started, to the analysis apparatus 6 via the communication unit 105. Then, the routine proceeds to a process in step S204.

(Step S204) The CPU 101 detects a turn timing of the wearer U, based on the acceleration detected by the acceleration sensor 107. The method of detecting the turn timing is the same as that in the first embodiment. Then, the routine proceeds to a process in step S205.

(Step S205) The CPU 101 determines whether or not the wearer U has touched a goal, based on the acceleration detected by the acceleration sensor 107. The method of determining a touch timing of the wearer U is the same as that in the first embodiment. The routine proceeds to a process in step S206 if the CPU 101 has determined that the wearer U touched a goal, and otherwise (if the CPU 101 has determined that the wearer U did not touch a goal), the routine returns to the process in step S204.

(Step S206) The CPU 101 transmits acceleration data indicating the acceleration detected by the acceleration sensors 106 to 108 during a period of time from the start timing to the touch timing, to the analysis apparatus 6 via the communication unit 105. At this time, the CPU 101 may transmit data indicating a start timing determined by the process in step S202, a turn timing determined by the process in step S204, and a touch timing determined by the process in step S205, along with the acceleration data, to the analysis apparatus 6. Then, the analysis process is ended.

Note that, in the present embodiment, the electronic device 1 transmits acceleration data during a period of time from the start timing to the touch timing, but the invention is not limited thereto. The electronic device 1 may transmit acceleration data during a period of time from the beginning of detection of acceleration to the touch, to the analysis apparatus 6. Alternatively, the electronic device 1 may begin transmission of acceleration data immediately after the start.

The analysis apparatus 6 switches the operation mode from the power saving mode to the normal mode when receiving a start signal. In general, a receiving sensitivity of the normal mode is higher than that of the power saving mode, in wireless communication. For this reason, the analysis apparatus 6 switches the operation mode from the power saving mode to the normal mode when receiving the start signal. Accordingly, the analysis apparatus 6 can improve the receiving sensitivity of the acceleration data transmitted in wireless communication.

The analysis apparatus 6 performs analysis processes such as estimating a swimming time, estimating a swim stroke, and estimating a frequency of stroke, based on the received acceleration data. Note that, in this embodiment, the analysis apparatus 6 performs estimating a swimming time, estimating a swim stroke, and estimating a frequency of stroke, but the invention is not limited thereto. The electronic device 1 may estimate the swimming time, estimate the swim stroke, and estimate the frequency of stroke.

As is described above, in the present embodiment, the electronic device 1 detects acceleration Y in a direction that becomes a gravity direction when the wearer U stands erect, and determines whether the wearer U is in a swimming state or the wearer U is in a resting state, based on the detected acceleration Y. Specifically, the electronic device 1 determines that the wearer U is in a resting state if the acceleration Y was within a predetermined range close to the acceleration of gravity for more than a predetermined length of time, and otherwise, determines that the wearer U is in a swimming state. Thereby, it is possible to accurately determine the swimming state and the resting state.

In addition, the electronic device 1 determines that a time when the absolute value of the acceleration Y becomes greater than a predetermined value immediately after the acceleration Y gets close to zero from the acceleration of gravity (1G or −1G) after having determined that the wearer U is in a resting state is a start timing. In addition, the electronic device 1 determines that a time when the absolute value of the acceleration Y becomes greater than a predetermined value during a period of time in which the electronic device 1 has determined that the wearer U is in a swimming state is a turn timing. Thus, because the start timing and the turn timing are identified based on the determination of the resting state or the swimming state, it is possible to further improve the accuracy to identify the start timing and the turn timing.

In addition, the electronic device 1 transmits a start signal to the analysis apparatus 6 when determining that the wearer U has started, and switches the operation mode of the analysis apparatus 6 to the normal mode. Then, the electronic device 1 transmits acceleration data to the analysis apparatus 6 when determining that the wearer U touched a goal. Thereby, the analysis apparatus 6 can receive the acceleration data with high sensitivity. Moreover, the analysis apparatus 6 can measure the consumption energy of the wearer U and the like, by estimating the swimming time and estimating the swim stroke.

In addition, entire functions or a portion of the functions of each of the units provided in the electronic device 1 and the analysis apparatus 6 according to the first embodiment and the second embodiment described above may be implemented by storing a program for performing these functions in a recording medium which is capable of being read by a computer, causing the program recorded in this recording medium to be read by a computer system, and executing the program. Note that, a 'computer system' described above includes hardware such as an OS (Operating System) and a peripheral device.

In addition, typically, a 'recording medium which is capable of being read by a computer' includes a portable medium like a flexible disc, an optical magnetic disc, a ROM, and a CD-ROM, or a storing unit such as a hard disc embedded in a computer system, however, the medium is not necessarily limited thereto.

Moreover, substituting a 'recording medium which is capable of being read by a computer', a medium which dynamically retains a program for a short period of time, like a communication wire used to transmit a program via a network such as the Internet or a communication line such as a telephone line, or a medium which retains a program for a certain period of time, like a volatile memory inside a computer system that becomes a server or a client in the aforementioned case, may also be included.

In addition, the program may be configured to implement a part of the functions described above. Furthermore, the program may be configured to implement the functions described above in combination with a program already recorded in the computer system.

The embodiments of the present invention are explained above. However, the technical scope of the present invention is not limited to the above-described embodiments, and a variety of modifications can be made to the above-described embodiments without departing from the scope of the present invention.

For example, in the above-described embodiment, an explanation is made as to a case where the electronic device 1 and the analysis apparatus 6 perform wireless communication. However, the transmitting and receiving of data between the electronic device 1 and the analysis apparatus 6 may be performed via a medium such as wire communication or a memory card.

In addition, in the above-described embodiment, an explanation is made as to a case where the electronic device 1 is attached to a breast portion. However, the position where the electronic device 1 is attached may be an upper body of the wearer U.

What is claimed is:

1. An analysis system comprising: an electronic device that is attached to an upper body of a swimmer; and an analysis apparatus,
wherein the electronic device comprises:
an acceleration sensor that detects acceleration in a direction that becomes a gravity direction when the swimmer stands erect; and
a first communication unit that transmits acceleration data indicating the acceleration detected by the acceleration sensor to the analysis apparatus,
and wherein the analysis apparatus comprises:
a second communication unit that receives the acceleration data from the electronic device; and
a state determination unit that determines whether a swimmer is in a swimming state or a swimmer is in a resting state, based on the acceleration data received by the second communication unit;
wherein the turn determination unit determines that a time when an absolute value of acceleration which is greater than a predetermined value is detected, is a timing when the swimmer performed a turn.

2. The analysis system according to claim 1, wherein the state determination unit determines that the swimmer is in a resting state if acceleration has been within a predetermined range close to the acceleration of gravity for more than a predetermined length of time, and otherwise, determines that the swimmer is in a swimming state.

3. The analysis system according to claim 1, wherein the analysis apparatus further comprises:
a turn determination unit that determines a timing when a swimmer performed a turn, from a time interval in which the state determination unit determined that a swimmer is in a swimming state, based on the acceleration data received by the second communication unit.

4. The analysis system according to claim 1, wherein the analysis apparatus further comprises:
a start determination unit that determines, based on the acceleration data received by the second communication unit, that a time when an absolute value of acceleration which is greater than a predetermined value is detected immediately after acceleration gets close to zero from the acceleration of gravity, is a timing when a swimmer started.

5. An analysis apparatus comprising:
a communication unit that receives, from a wearable electronic device including an acceleration sensor which detects acceleration in a direction that becomes a gravity direction when a wearer of the electronic device stands erect, acceleration data indicating acceleration detected by the acceleration sensor;
a state determination unit that determines whether a wearer is in a swimming state, or in a resting state, based on the acceleration data received by the communication unit; and
a turn determination unit that determines that a time when an absolute value of acceleration which is greater than a predetermined value is detected, is a timing when a swimmer performed a turn.

6. A wearable electronic device, the device comprising:
a plurality of acceleration sensors that detect the X component, the Y component, and the Z component of orthogonal coordinate axes that are orthogonal to one another, and output an acceleration signal with an intensity corresponding to the acceleration of each of the components, wherein the acceleration sensors are arranged in three axes directions that are orthogonal to one another and one of the three axes directions includes an axis in a direction that becomes a gravity direction when a wearer of an electronic device stands erect; and
wherein the position of the acceleration sensors is displaced to any one of a left side and a right side from the center of a breast portion of a wearer;
a processing unit;
a storing unit that stores programs executed by the processing unit and acceleration data indicating acceleration detected by the acceleration sensors;
wherein the programs comprise a program for determining whether a wearer is in a swimming state, or in a resting state, based on acceleration detected by the acceleration sensor;
wherein the processing unit further executed the program to determine that a time when an absolute value of acceleration which is greater than a predetermined value is detected, is a timing when the swimmer performed a turn.

7. An analysis method in an analysis system provided with an electronic device attached to an upper body of a swimmer and an analysis apparatus, the method comprising:
a step in which the electronic device detects acceleration in a direction that becomes a gravity direction when a swimmer stands erect;
a step in which the electronic device transmits acceleration data indicating detected acceleration to the analysis apparatus;
a step in which the analysis apparatus receives the acceleration data from the electronic device;
a step in which the analysis apparatus determines whether a swimmer is in a swimming state or a swimmer is in a resting state, based on the received acceleration data; and
a step in which the analysis apparatus determines that a time when an absolute value of acceleration which is greater than a predetermined value is detected, is a timing when the swimmer performed a turn.

8. An analysis method in a wearable electronic device, the method comprising:
a detecting step in which the electronic device detects acceleration in a direction that becomes a gravity direction when a wearer of an electronic device stands erect; and
an execution step in which the electronic device executes a program that determines whether wearer is in a swimming state or a wearer is in a resting state, based on detected acceleration;
wherein the execution step further determines that a time when an absolute value of acceleration which is greater than a predetermined value is detected, is a timing when the swimmer performed a turn.

9. A non-transitory storage medium that stores a program for causing a computer as an analysis apparatus to execute:
a step of receiving, from a wearable electronic device that is worn by a swimmer and is provided with an acceleration sensor which detects acceleration in a direction that becomes a gravity direction when a swimmer stands erect, acceleration data indicating acceleration detected by the acceleration sensor; and
a step of determining whether a swimmer is in a swimming state, or in a resting state, based on the received acceleration data;
wherein the step of determination further comprises determining that a time when an absolute value of acceleration which is greater than a predetermined value is detected, is a timing when the swimmer performed a turn.

10. A non-transitory storage medium that stores a program for causing a computer as a wearable electronic device by a swimmer to execute:
a step of detecting acceleration in a direction that becomes a gravity direction when a swimmer stands erect; and
a step of determining whether a swimmer is in a swimming state or a swimmer is in a resting state, based on detected acceleration;
wherein the step of determination further comprises determining that a time when an absolute value of acceleration which is greater than a predetermined value is detected, is a timing when the swimmer performed a turn.

11. An analysis system comprising: an electronic device that is attached to an upper body of a swimmer; and an analysis apparatus,
wherein the electronic device comprises:
an acceleration sensor that detects acceleration in a direction that becomes a gravity direction when a swimmer stands erect; and
a first communication unit that transmits acceleration data indicating acceleration detected by the acceleration sensor to the analysis apparatus,
and wherein the analysis apparatus comprises:
a second communication unit that receives the acceleration data from the electronic device; and
a touch determination unit that, based on the acceleration data received by the second communication unit, traces back the received acceleration data from a predetermined timing and thereby determines a timing when a swimmer touched a goal.

12. The analysis system according to claim 11, wherein the touch determination unit traces back the received acceleration data from a time when acceleration becomes close to the acceleration of gravity, and thereby determines that a time when acceleration becomes equal to or less than a predetermined value is the timing when a swimmer touched a goal.

13. The analysis system according to claim 12, wherein the analysis apparatus further comprises a state determination unit that determines whether a swimmer is in a swimming state or a swimmer is in a resting state, based on the acceleration data received by the second communication unit, and wherein
the touch determination unit traces back the received acceleration data from a time when a swimmer shifted from a swimming state to a resting state, and thereby determines that a time when acceleration becomes equal to or less than a predetermined value is the timing when a swimmer touched a goal.

14. An analysis apparatus comprising:
a communication unit that receives, from an electronic device that is attached to an upper body of a swimmer and is provided with an acceleration sensor which detects acceleration in a direction that becomes a gravity direction when a swimmer stands erect, acceleration data indicating acceleration detected by a acceleration sensor; and
a touch determination unit that, based on the acceleration data received by the communication unit, traces back the received acceleration data from a predetermined timing and thereby determines a timing when a swimmer touched a goal.

15. An electronic device that is attached to an upper body of a swimmer, the device comprising:
an acceleration sensor that detects acceleration in a direction that becomes a gravity direction when a swimmer stands erect; and
a touch determination unit that, based on acceleration detected by the acceleration sensor, traces back the detected acceleration from a predetermined timing and thereby determines a timing when a swimmer touched a goal.

16. An analysis method in an analysis system provided with an electronic device attached to an upper body of a swimmer and an analysis apparatus, the method comprising:
a step in which the electronic device detects acceleration in a direction that becomes a gravity direction when a swimmer stands erect;
a step in which the electronic device transmits acceleration data indicating detected acceleration to the analysis apparatus;
a step in which the analysis apparatus receives the acceleration data from the electronic device; and
a step in which the analysis apparatus, based on the received acceleration data, traces back the acceleration data from a predetermined timing and thereby determines a timing when a swimmer touched a goal.

17. An analysis method in an electronic device attached to an upper body of a swimmer, the method comprising:
a step in which the electronic device detects acceleration in a direction that becomes a gravity direction when a swimmer stands erect; and
a step in which the electronic device, based on detected acceleration, traces back the detected acceleration from a predetermined timing and thereby determines a timing when a swimmer touched a goal.

18. A non-transitory storage medium that stores a program for causing a computer as an analysis apparatus to execute:
a step of receiving, from an electronic device that is attached to an upper body of a swimmer and is provided with an acceleration sensor which detects acceleration in a direction that becomes a gravity direction when a swimmer stands erect, acceleration data indicating acceleration detected by the acceleration sensor; and
a step of, based on the received acceleration data, tracing back the received acceleration data from a predetermined timing and thereby determining a timing when a swimmer touched a goal.

19. A non-transitory storage medium that stores a program for causing a computer as an electronic device attached to an upper body of a swimmer to execute:
a step of detecting acceleration in a direction that becomes a gravity direction when a swimmer stands erect; and
a step of, based on detected acceleration, tracing back the detected acceleration from a predetermined timing and thereby determining a timing when a swimmer touched a goal.

* * * * *

UNITED STATES PATENT AND TRADEMARK OFFICE
CERTIFICATE OF CORRECTION

PATENT NO. : 9,192,843 B2
APPLICATION NO. : 14/011392
DATED : November 24, 2015
INVENTOR(S) : Keisuke Tsubata et al.

It is certified that error appears in the above-identified patent and that said Letters Patent is hereby corrected as shown below:

In the Claims

In column 13, claim 1, line 22, after "a timing when" replace "the" with --a--.

In column 14, claim 6, line 16, after "unit further" replace "executed" with --executes--.

In column 14, claim 6, line 19, after "a timing when" replace "the" with --a--.

In column 14, claim 7, line 39, before "swimmer performed" replace "the" with --a--.

In column 14, claim 8, line 47, after "determines whether" insert --a--.

In column 14, claim 8, line 53, before "swimmer performed" replace "the" with --a--.

In column 15, claim 9, line 2, after "a timing when" replace "the" with --a--.

In column 15, claim 10, line 15, after "a timing when" replace "the" with --a--.

In column 15, claim 14, line 60, after "acceleration detected by" replace "a" with --the--.

Signed and Sealed this
Fifth Day of April, 2016

Michelle K. Lee
*Director of the United States Patent and Trademark Office*